(12) United States Patent
Rovira et al.

(10) Patent No.: US 9,289,172 B2
(45) Date of Patent: Mar. 22, 2016

(54) OPTOELECTRONIC DEVICE FOR THE DETECTION OF UTERINE CERVICAL CANCER, COMPRISING A SELF-POSITIONING ATTACHMENT

(71) Applicant: Instituto Tecnologico y de Estudios Superiores de Monterrey, Monterrey, N.L (MX)

(72) Inventors: Noel Leon Rovira, Nuevo Leon (MX); Arturo Hernandez Fuentes, Coahuila (MX); Jose Antonio Viornery Escorza, Hidalgo (MX); Norma Frida Roffe Samaniego, Nuevo Leon (MX)

(73) Assignee: Instituto Tecnologico y de Estudios Superiores de Monterrey, Monterrey, N.L. (MX)

( * ) Notice: Subject to any disclaimer, the term of this patent is extended or adjusted under 35 U.S.C. 154(b) by 0 days.

(21) Appl. No.: 14/573,783

(22) Filed: Dec. 17, 2014

(65) Prior Publication Data

US 2015/0105669 A1    Apr. 16, 2015

Related U.S. Application Data

(63) Continuation of application No. 13/409,088, filed on Feb. 29, 2012, now abandoned, which is a continuation of application No. 11/574,705, filed as application No. PCT/MX2006/000011 on Feb. 20, 2006, now abandoned.

(30) Foreign Application Priority Data

Feb. 21, 2005  (MX) ..................... NL/a/2005/000016
Mar. 1, 2005   (MX) ..................... NL/a/2005/000018

(51) Int. Cl.
*A61B 5/053* (2006.01)
*A61B 6/00* (2006.01)
(Continued)

(52) U.S. Cl.
CPC .............. *A61B 5/4331* (2013.01); *A61B 5/0059* (2013.01); *A61B 5/0084* (2013.01); *A61B 5/053* (2013.01); *A61B 5/4325* (2013.01); *A61B 2010/0216* (2013.01)

(58) Field of Classification Search
None
See application file for complete search history.

(56) References Cited

U.S. PATENT DOCUMENTS 3,995,618 A   12/1976   Kingsley et al.
4,458,694 A   7/1984    Sollish et al.
(Continued)

FOREIGN PATENT DOCUMENTS

AU    B-516114    5/1981
DE    221635      5/1985
(Continued)

OTHER PUBLICATIONS

International Search Report; PCT/MX2006/000011; Jun. 29, 2006; 11 pp.
(Continued)

*Primary Examiner* — Long V Le
*Assistant Examiner* — Bradley Impink
(74) *Attorney, Agent, or Firm* — Fish & Richardson P.C.

(57) ABSTRACT

The present invention relates to a portable device which analyzes cervical tissue using two simultaneous measurements, namely an electrical measurement and an optical measurement. The aforementioned device examines different areas of cervical tissue, taking electrical measurements from same in different frequency ranges and optical measurements in three different wavelengths. Once the measurements have been obtained, they are processed by a configurable device or microcontroller in accordance with mathematical formulae obtained from multiple measurements taken from healthy and cancerous tissues. Three possible responses can be obtained from the processing of the measurements: healthy tissue, cancerous tissue or the presence of human papilloma virus. The inventive device can be used as a self-detection device since it is equipped with an attachment for positioning same upon detection of proximity to the cervix in order to take a correct measurement. The aforementioned attachment also comprises an accessory which can be used to perform the alternative method in which a cell sample is taken and sent for laboratory analysis in order to obtain an immediate response, which can be used by the user or by another person. The purpose of the invention is to provide a minimally-invasive diagnostic device for Papanicolaou testing and to offer an alternative method to the examination that requires the taking of a cell sample.

5 Claims, 9 Drawing Sheets

(51) Int. Cl.
  *A61B 5/00* (2006.01)
  *A61B 10/02* (2006.01)

(56) References Cited

U.S. PATENT DOCUMENTS

| | | |
|---|---|---|
| 4,498,481 A | 2/1985 | Lemeke |
| 4,762,133 A | 8/1988 | Bayne et al. |
| 5,231,992 A | 8/1993 | Leon |
| 5,353,802 A | 10/1994 | Ollmar |
| 5,361,762 A | 11/1994 | Gunter |
| 5,439,000 A | 8/1995 | Gunderson et al. |
| 5,503,853 A | 4/1996 | Bollen et al. |
| 5,792,053 A | 8/1998 | Skladnev et al. |
| 5,855,551 A | 1/1999 | Sklandnev et al. |
| 5,941,822 A | 8/1999 | Skladney et al. |
| 6,026,323 A * | 2/2000 | Skladnev et al. ............ 600/547 |
| 6,155,990 A | 12/2000 | Fournier |
| 6,169,914 B1 | 1/2001 | Hovland et al. |
| 6,302,853 B1 | 10/2001 | Sak |
| 6,402,700 B1 | 6/2002 | Richards |
| 6,719,687 B1 | 4/2004 | Van Der Weegen |
| 6,832,111 B2 | 12/2004 | Tu et al. |
| 6,845,264 B1 * | 1/2005 | Skladnev et al. ............ 600/547 |
| 2004/0116827 A1 | 6/2004 | Tiberio |
| 2005/0029437 A1 | 2/2005 | Hasegawa et al. |
| 2005/0165326 A1 | 7/2005 | Kirsner |

FOREIGN PATENT DOCUMENTS

| | | |
|---|---|---|
| EP | 0650694 | 5/1995 |
| EP | 0865761 | 8/1997 |
| EP | 0872211 | 8/1997 |
| EP | 1462057 | 9/2004 |
| GB | 2159240 | 11/1985 |
| JP | 2000109743 | 4/2000 |
| WO | 9841281 | 9/1998 |

OTHER PUBLICATIONS

Brown et al.; "Relation between Tissue Structure and Imposed Electrical Current Flow in Cervical Neoplasia"; The Lancet, vol. 355, Mar. 2000; pp. 892-895.

* cited by examiner

OPTOELECTRONIC DEVICE FOR THE DETECTION OF UTERINE CERVICAL CANCER, COMPRISING A SELF-POSITIONING ATTACHMENT

BACKGROUND OF THE INVENTION

The identification of various kinds of tissues is based on their response both to an electrical stimulus and the response to light incidence. There are currently many apparatus and techniques for identifying different kinds of tissues, both normal and tissues infected with human papilloma virus, precancerous and cancerous. Many Optical principles exist which are already tested for identifying tissues such as Spectroscopic Fluorescence, Raman Spectroscopy and OCT. On other hand biological tissues have a characteristic electrical impedance which is related to the frequency in that the tissue has components having both resistive and charge storing (capacitive) characteristics. Impedance magnitude and its dependence on the frequency are a function of the tissue composition.

The starting point of this invention focuses in the fact that no uterine cervical cancer detection method displays a sufficiently precise reliability, which gives a high risk of an erroneous diagnosis, this turning into a very important matter if we understand that this type of cancer can be cured if it detected at an early stage, otherwise being mortal.

The conventional Papanicolau or uterine cervical cancer testing has been practically the same since about 60 years. Since 1940 the death percentage in women having cervical cancer has decreased 70%, mainly because many women undergo Papanicolau testing or uterine cervical cancer tests. Although not infallible, this test detects 95% of cervical cancers and, more importantly, it detects them in a state which is not visible to the naked eye yet and, therefore, they can be treated and almost invariably cured. Despite the increase in worldwide opportune uterine cervical cancer detection campaigns by the Papanicolau testing, in some countries, specially those of the third world or undeveloped ones, there are still strong cultural and psychological barriers in women and occasionally in their couples which cause women not to undergo a Papanicolau testing.

Among some of these barriers there are wrong beliefs, fear to obtain an adverse result, to the pain in the examination or shyness as the examination could be undertaken by a male person or in the presence of strange persons in an assisting facility.

Currently there has been uncountable optical, electrical and biomedical research, and further each one of them has different variants. For instance the review article "Relation between tissue structure and imposed electrical current flow in cervical neoplasia" relates to studies performed on the cervix tissue reaction when electrical pulses are applied at different frequency ranges. This article discloses a thorough research of every part intervening in this invention, particularly on the electrical measurement, optical measurement, the electronics inside the device and the assembly materials.

Inventions currently exist that use electrical impedance measurement from tissue. Representative patents are: U.S. Pat. No. 4,458,694, "Apparatus and method for detection of tumors in tissue"; U.S. Pat. No. 5,353,802, "Device for measurement of electrical impedance of organic and biological materials"; U.S. Pat. No. 5,361,762, "Apparatus for detecting properties, differences and changes of humans or animals bodies"; and U.S. Pat. No. 6,026,323, "Tissue diagnostic system". In relation to the optical part based on the methods of light reflection from tissues the representative patents are the following: U.S. Pat. No. 4,930,516, "Method for detecting cancerous tissue using visible native luminescence"; U.S. Pat. No. 5,503,853, "Use of light conveyed by fiber optics to locate tumors. Physiological probe"; U.S. Pat. No. 5,439,000, "Method of diagnostic tissue with guidewire", and U.S. Pat. No. 6,026,323, "Tissue diagnostic system".

With respect to self-detection devices, some important inventions have been found. U.S. Pat. No. 3,995,618 to Kingsley et al. claims a cervical sample collecting device which can be self-administered comprising an outer tube and an inner tube telescopically positioned inside the outer tube, a wet cervical sponge having a setting solution and mounted in the front end portion of the inner tube and projecting outwardly from it and a protecting sleeve which surrounds the inner tube and the cervical sponge before and after its insertion into the vagina.

U.S. Pat. No. 5,231,992 claims a device for self-obtaining cervix cell and fluid samples comprising a cervical cell and fluid collector, formed of a disc shaped body manufactured from a polyurethane foam which is placed in the patient's cervix and fluids and cells adhere to the device walls.

U.S. Pat. No. 6,155,990 to Fournier claims a device for auto-sampling culture material or specimens used in cytological or microbiological study techniques, which comprises a cardboard tube housing a retractable sponge that includes a grip adapted for serving as a screwable cap for sealing and preserving a sample within a tube.

U.S. Pat. No. 6,302,853 to Sak, Robert F. claims a device and method for collecting cervical tissue samples comprising an insertion tube and an introduction guide member which guides the insertion tube into the vaginal cavity. A cervical sample collector is included that is positioned inside the vaginal insertion tube and extends into the vaginal cavity for collecting the sample, which has to be rotated until completing a revolution.

U.S. Pat. No. 6,402,700 to Richards, claims an personal apparatus and method for taking cervical cell samples that includes an insertion handle, a flexible speculum ring and means for movably attaching the speculum ring to the insertion handle. The speculum ring includes two adjacent ring halves circumferentially divided in order to allow the expansion of the speculum tube housed inside the hollow ring halves. The method comprises inserting the flexible speculum assembly inside user's vagina, moving the speculum ring into a raised position surrounding the cervix, separating the ring halves for expanding the tube, defining an speculum aperture and inserting a sampling tool through the orifice until it contacts the cervix or the surface of the areas adjacent thereto.

Australian Patent No. A61B 10/00 discloses a device for cervical tissue sample collection comprising a cylindrical barrel with an inner shaft. Said shaft has in its one end a circular brush and a sponge. The device is introduced in the vagina, and once it is inside the shaft is pushed and the end is rotated. The sponge and brush will collect a sample of the tissues. Once the process has ended, the shaft end wherein the brush and sponge are located can be detached and sent to analysis.

British Patent No. GB 2159240 teaches a method for obtaining cervical canal cells by inserting a conical shaped brush for trapping the cells therein.

The main disadvantage of these devices claimed by all the above disclosed patents resides in the fact that the user cannot achieve a correct localization of the cervix, therefore the sample is taken from wrong places consequently obtaining very poor quality samples which are inadequate for their analysis, thus causing the need of repeating the test or that the user has to attend an specialist.

From the above disclosure, a need has been found for having a device which relies in the correct positioning and locating of the cervix and that also does not always uses an invasive method based on the retrieval and sample collection of the cervix, and that this new device by means of an accurate localization of the cervix performs simultaneous electrical and optical tissue measurements, and in the case of the test resulting positive to cancer this same device by means of an attachment retrieves the tissue samples in order for them to be sent to a laboratory and follow the common procedure. Other advantage of this invention is that the user has the choice of performing the detection test without requiring the presence of a skilled physician.

BRIEF DISCLOSURE OF THE DRAWINGS

The drawings herein attached are briefly disclosed in the following.

DISCLOSURE OF THE INVENTION

Figure 1:
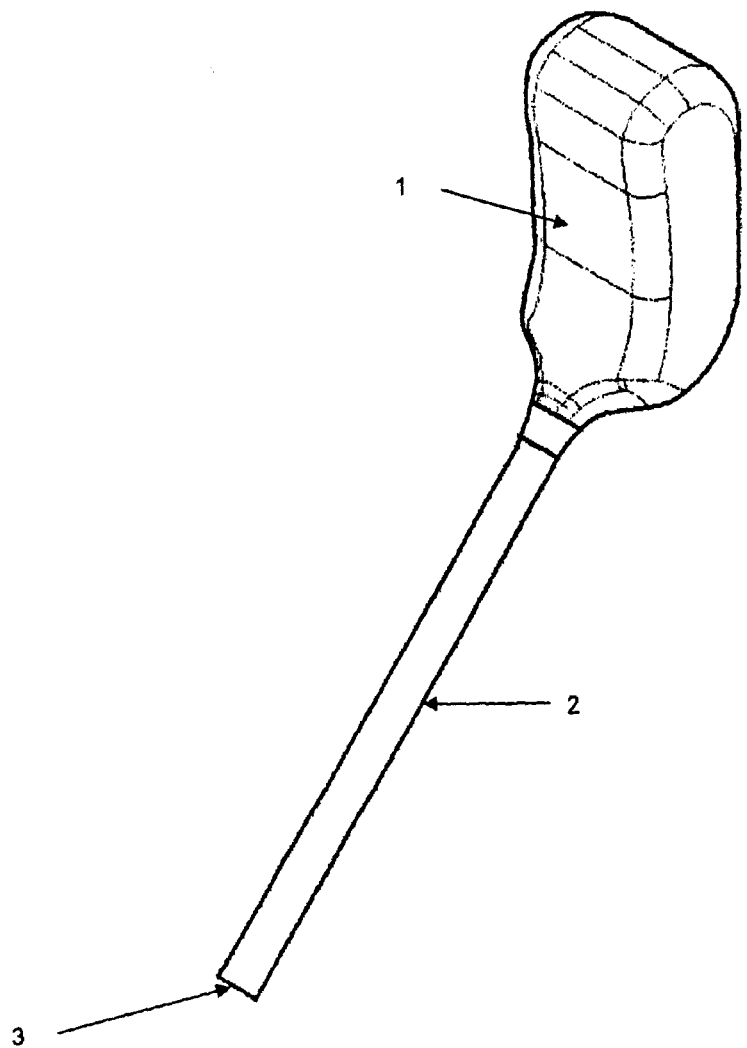
FIG. 1 shows an schematic view of the present invention apparatus.
Figure 2:
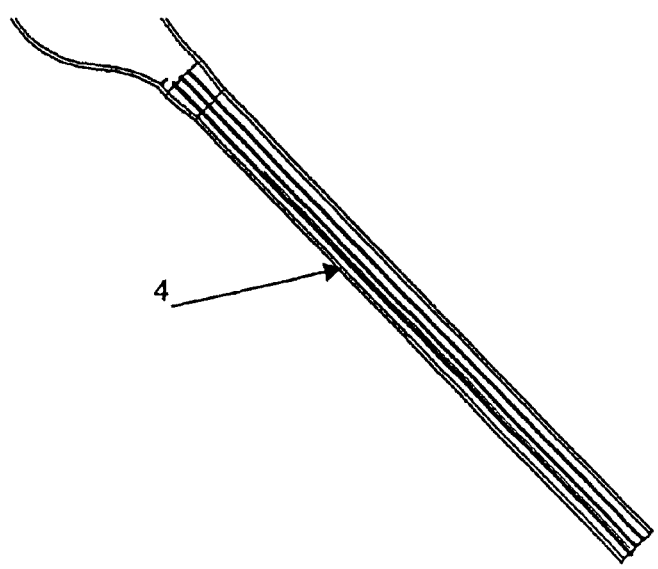
FIG. 2 shows a side view of the test piece used in the present invention.
Figure 3:
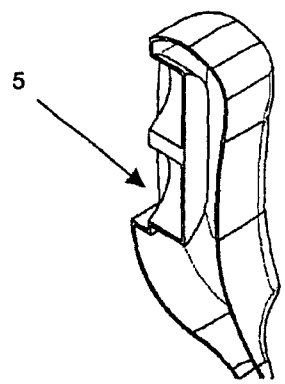
FIG. 3 depicts an isometric cross-section view of the casing or handle used in the present invention.
Figure 4:
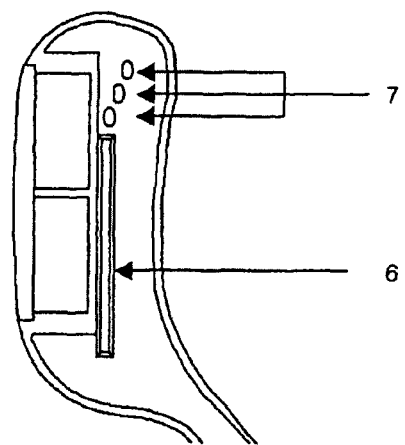
FIG. 4 depicts a cross-section view of the casing or handle used in the present invention.
Figure 5:
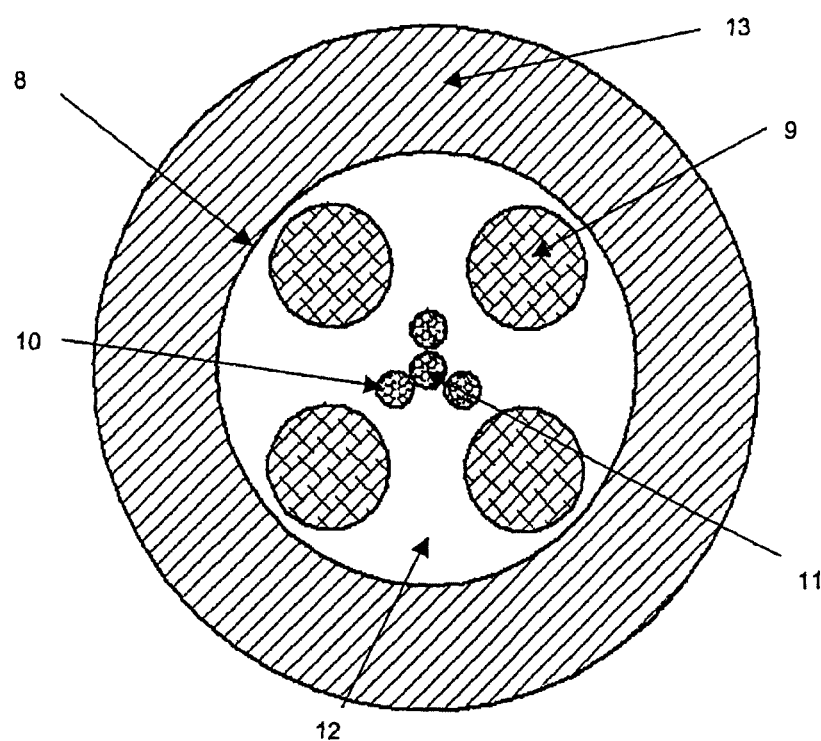
FIG. 5 shows a view of the test tube making contact with the cervix in the present invention.
Figure 6:
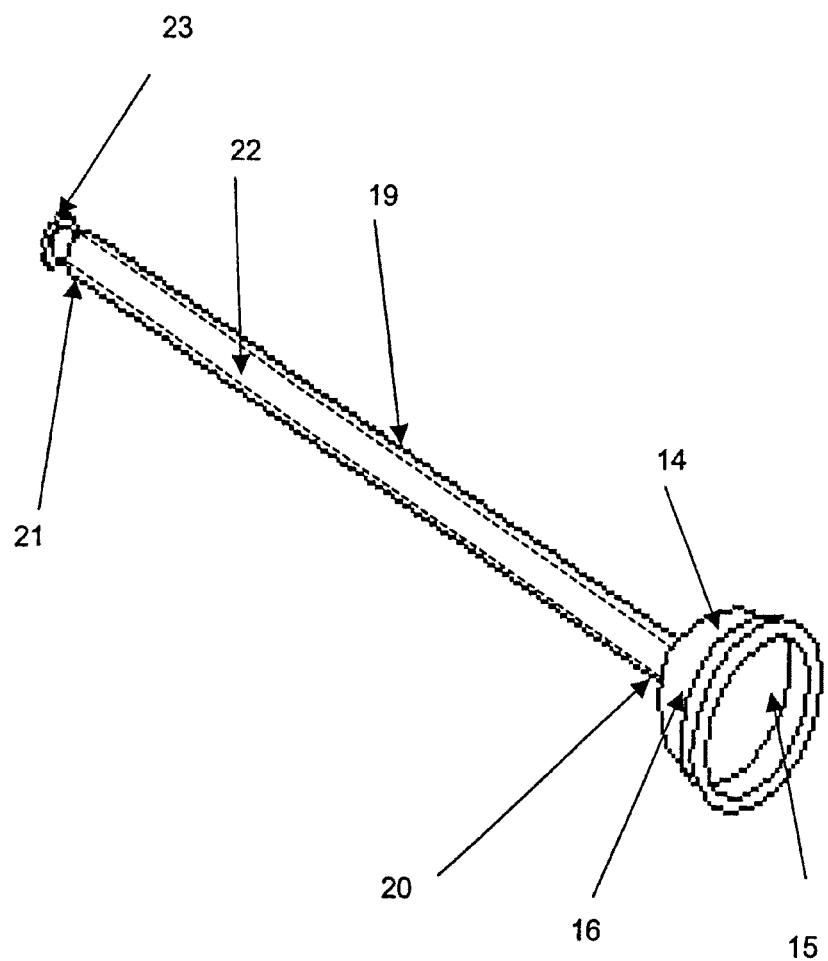
FIG. 6 is an schematic view of the assembled positioning attachment.
Figure 7:
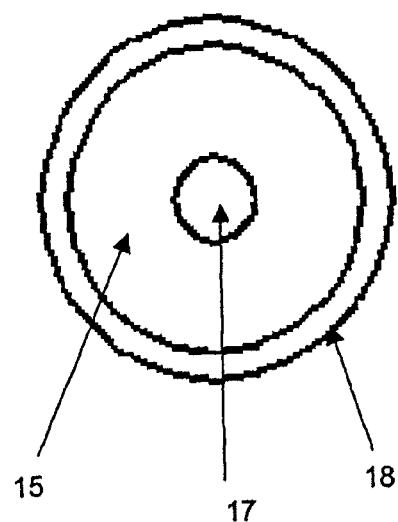
FIG. 7 is a top view of the positioning attachment.

The invention presented in this document is a novel system designed for detecting cancer, precancer and human papilloma virus.

The device is a portable uterine cervical cancer detection optoelectronic system. It is an instrument manipulated by the physician or its user and displays a real time result, being optional the collection of physical tissue samples for testing. In its outer part the present invention consists of three main components, being the first one the casing (1) inside of which it is located the whole electronic part of the system which rests on a printed card containing the necessary LEDs for optical measurement, as well the photodiodes for receiving the luminous reflection from the cells; the printed card also contains a microcontroller or configurable device that has several functions, on of them being the sending of signals amplified by operational amplifiers for the electrical stimulation of the cells; an interface receiving the signals from the diodes and electrodes for performing an analog-to-digital conversion and sending them to the microcontroller or configurable device in order for it to read the collected measurements to give a response which will be instantly displayed in light indicators; the second part is the test tube (2) through which the fiber optics wiring (4) pass that are needed for transmitting the light outputs and inputs; on other hand there is the test tube tip (3) in which the output (10) and input (11) fiber optics are located, also the gold electrodes which generate the current and perform electrical measurements (9). The fibers are sandwiched in an epoxy resin (12) which protects the wiring throughout the test tube manufactured from a sterilizable plastics material preferably Ultem (8). Outside the test tube a disposable cover (13) is disposed for the hygienic reutilization of the device.

The positioning attachment consists of a circular member (14) of flexible medical grade plastic in the shape of a diaphragm, including an internal concave surface (15), an external surface (16), a bore (17) on its center portion and a circular ring (18) of the same material depending on its periphery. It also contains a flexible guide member comprising a flexible plastic tube (19) with a diameter similar to that of the center bore (17) of the diaphragm shaped circular member (14), having a first end (20) joined to the center portion of the positioning member, matching the center bore thereof and depending from its outer surface, and a second end (21). Finally, it has a rigid, hollow guide member (22) with a diameter lesser than the flexible plastic tube (19) of the positioning member, having first and second ends and a plastic ring (23) joined to its second end (21).

Figure 8:
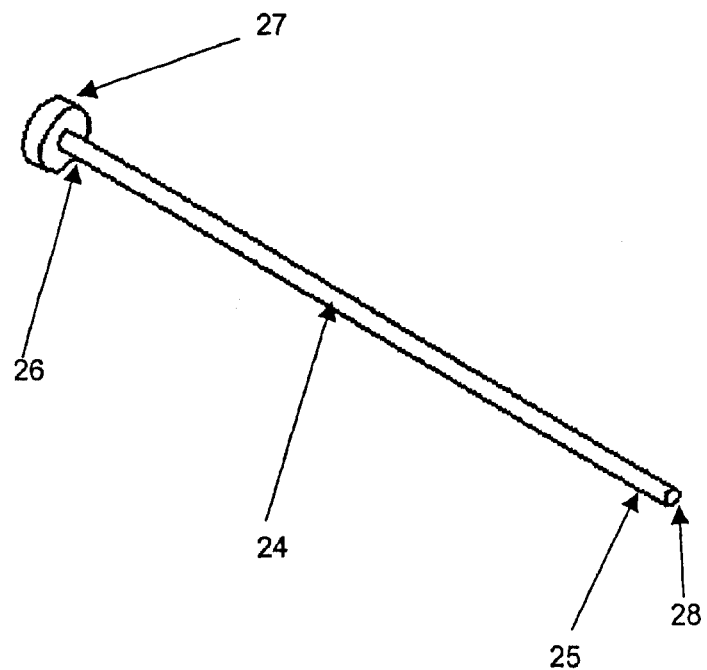
FIG. 8 is an schematic view of the sample collecting attachment.

The sample collecting attachment, shown in FIG. 8, consists of a sample collection solid rigid plastic tube (24) having a diameter lesser than the rigid guide member, having a first (25) and second (26) end, wherein the second end includes a plastic ring (27) joined to the second end (26) as an auxiliary grip which allows to easily handle and rotate the sample collection rigid tube, and three cytological scraping brushes (28) equidistantly joined to the first end of the rigid tube at an angle of about 15 grades to a vertical reference axis of the rigid tube.

Figure 9:
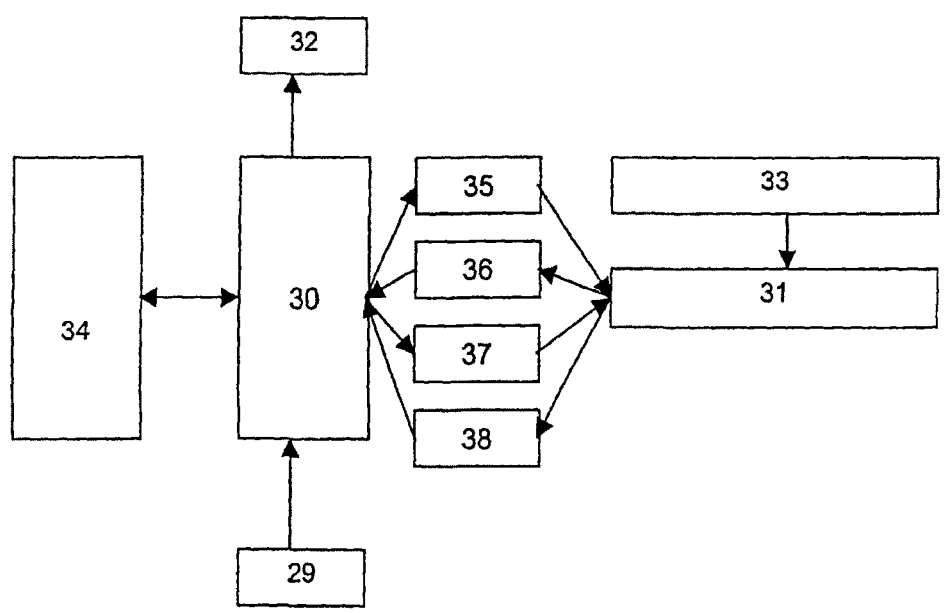
FIG. 9 is a block diagram showing the operation of the present invention device.

The user begins the testing for uterine cervical cancer detection by means of the control panel (29) which performs the general turning on and off functions. The operation of the device actuates the electrical and optical stimulation by sending the corresponding signals and performing the measurements. Signal sending and processing of the measurement data retrieved in the different measurements are performed in an electronic card (6) which contains the processing unit implemented by a microcontroller or configurable circuit. This processing unit sends the optical signals through the light emitting circuit (35) and the electrical signals through the current injection circuit (37). The central processing unit receives the resulting luminance through the light receiving circuit (36), and the voltage present in the tissue through the voltage measuring circuit (38) and stores them in the storage system (34). With the measurements captured from the signals received by these data, the condition of the tissue is calculated and the result is delivered in real time by the three outer LEDs (7 and 32) (wherein a green LED indicates that the person is healthy, a yellow LED indicates the presence of human papilloma virus, and a red LED indicating the presence of cancerous cells). In FIG. 9 the device block diagram can be observed, which apart from the aforementioned components, shows the test tube (31) and positioning attachment (33).

Figure 10:
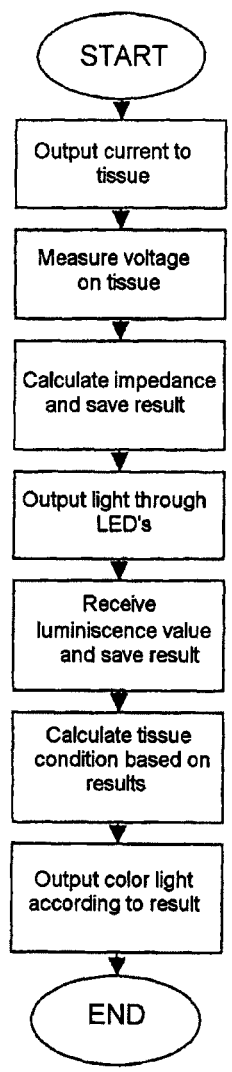
FIG. 10 is a flowchart showing the operation of the device.

FIG. 10 depicts a flowchart explaining the device operation. As seen in the chart, the cancer detection process is automated and executed in real time, thus providing instant results, which is very convenient for self-detection.

The physician or user performing the testing passes the tip of the test tube through the cervix where the measurements are done by using electrical pulses at different frequencies, as well as light pulses in three different wavelengths.

The readings obtained from the measurements are processed in the microcontroller or configurable device according to mathematical formulae, which were designed from tests performed on healthy and cancerous tissue in order for the detection to be possible. The processing outcome is the classification of the measurements as normal (green LED) or abnormal (yellow or red LED). When an abnormality is found on a sample there are two possible causes and actions: Presence of human papilloma virus (yellow LED lights up), presence of cancer cells (red LED lights up).

This invention provides as main feature that it is an instrument capable of taking two simultaneous measurements, the electrical and the optical ones, from very small tissue sections, in that currently there are no evidences that the tests are affected each other.

Moreover, the device posses an attachment that can be used for performing a self-detection, that is, the person itself can perform the cervical cancer test without needing help from other person, and thus the above explained differs from all the up to now patented devices such as the one entitled "Hybrid probe for tissue type recognition", that entitled "Apparatus for tissue type recognition within a body canal", that entitled "Integral sheathing apparatus for tissue recognition probes", and that entitled "Tissue diagnostic system".

The invention consists of the sequence of tests performed by the two electrical and optical measurement methods; in order for the tests to be adequately performed the tip of the test tube needs to contact the patient cervix, it is important that the measurement is taken through the whole cervix in order to have a significant measurement of all the tissues.

In the case of the electrical part, the current is applied to the surface and the same does not necessarily expands through the surface of the tissue but it penetrates therein to a certain depth. The features of the electrical impedance of the tissues can be explained by changes in cell arrangements and the size of the nucleus. This relation constitutes the basis for knowing the tissue structure starting from the electrical impedance spectrum measurements, that is to say, this pattern will serve us to differentiate normal tissues from precancerous ones. The main changes in precancerous tissue occur by the subdivision in the surface cell layers and there also occurs an increase in the nucleus size. The proposed method is performed with a test tube of about 4.0-7.0 mm. diameter, with four gold electrodes of 0.8-1.2 mm. diameter, spaced each other by a middle circle of 1.5-2.0 mm., applying a 10 μA peak to peak current at several frequencies. The condition of the tissue is related to the frequency in that the tissue has components having both resistive and charge storage (capacitive) characteristics. The magnitude of the impedance and its dependence on the frequency are a function of the tissue composition. The measurement is performed with the same electrodes located in the test tube.

In the case of the optical part, three different wavelengths are output and the luminance with which each of them returns is received. Because the size of the test tube is so reduced the transmission is done throughout the whole test tube by means of fiber optics, these fibers being connected to the three. LEDs for outputting the signal, whereas for performing the reading there is a photodiode also connected to the fiber optics, then the signal is digitalized and the comparison is made, thus subsequently sending the signal whether normal or abnormal for displaying the final result to the user by means of three LEDs.

The best method for both measurements to be successfully performed requires a series of steps which will now be disclosed briefly and in order: Placing the tip of the test tube on the cervix and performing a scanning or sweep therethrough; performing the electrical stimulation and sending the optic pulses; receiving the measurement of impedance value and light intensities, digitizing the signal; processing the measurements by comparing them to values previously obtained and synthesized in a mathematical formula and obtaining an instant response. It is advisable to make a scanning on the cervix from between one and two minutes in order to obtain a reliable measurement.

What is claimed is:

1. A portable device for self-diagnosis test of cervical cancer tissue, the portable device comprising:
    a test tube comprising, in a proximal tip, electrodes to transmit electrical current to the tissue and receive a tissue electrical voltage produced by the applied electric current, a plurality of emitting optical fibers to transmit light pulses to the tissue, and a plurality of receiving optical fibers to pick up the light intensity of the tissue produced by the light pulse;
    a distal housing and the test tube forming a single body, the distal housing including operational amplifiers to generate and regulate the electrical current transmitted to the tissue through the electrodes of the test tube, inner LEDs to generate the light pulse transmitted to the tissue through the emitting optical fibers of the test tube, photodiodes to sense the light intensity of tissue from the receiving optical fibers of the test tube, and a microcontroller operatively connected to the operational amplifiers, to the inner LEDs, to the photodiodes, and to the electrodes; and
    a plurality of outer LEDs connected to the microprocessor, wherein the plurality of outer LEDs are positioned on a surface of the distal housing to present a signal such that the signal presented by the outer LEDs is visible to a user performing the self-diagnosis test of cervical cancer tissue using the portable device;
    wherein the microcontroller receives the electrical voltage and light intensity of the tissue through the electrodes and photodiodes respectively to determine the impedance and light intensity values of the tissue, compares the impedance and light intensity values of the tissue to stored and preset tissue impedance and light intensity values, and triggers the outer LEDs to present the signal indicative of a test result.

2. The portable device according to claim 1, wherein the electrical current transmitted to the tissue is of 10 μA peak to peak.

3. The portable device according to claim 1, wherein a first outer LED is of green color to present a signal indicative of normal tissue, a second outer LED is of red color to present a signal indicative of abnormal tissue, and a third outer LED is of yellow color to present a signal indicative of abnormal tissue.

4. The portable device according to claim 3, wherein the signal presented by the second outer LED is indicative of cancerous cells being present in the tissue.

5. The portable device according to claim 3, wherein the signal presented by the third outer LED is indicative of human papilloma virus being present in the tissue.

* * * * *